US011382565B2

(12) United States Patent
Harris et al.

(10) Patent No.: US 11,382,565 B2
(45) Date of Patent: Jul. 12, 2022

(54) OPTOACOUSTIC PROBE

(71) Applicant: Seno Medical Instruments, Inc., San Antonio, TX (US)

(72) Inventors: Jeffrey Nelson Harris, San Antonio, TX (US); Tam Thien Do, San Antonio, TX (US); Xavier Rey Saenz, San Antonio, TX (US); Lisa Michelle Richards Cook, San Antonio, TX (US)

(73) Assignee: Seno Medical Instruments, Inc., San Antonio, TX (US)

( * ) Notice: Subject to any disclaimer, the term of this patent is extended or adjusted under 35 U.S.C. 154(b) by 275 days.

(21) Appl. No.: 16/517,831

(22) Filed: Jul. 22, 2019

(65) Prior Publication Data

US 2021/0022680 A1    Jan. 28, 2021

(51) Int. Cl.
*A61B 5/00* (2006.01)
*G01N 29/24* (2006.01)
*A61B 5/103* (2006.01)

(52) U.S. Cl.
CPC .......... *A61B 5/6844* (2013.01); *A61B 5/0095* (2013.01); *A61B 5/1032* (2013.01); *A61B 5/443* (2013.01); *G01N 29/2418* (2013.01)

(58) Field of Classification Search
CPC ..... A61B 5/6844; A61B 5/1032; A61B 5/443; A61B 5/0095; A61B 5/0091; G01N 21/1702; G01N 29/2418; G01N 2021/1706
See application file for complete search history.

(56) References Cited

U.S. PATENT DOCUMENTS

| 2013/0116538 A1* | 5/2013 | Herzog | A61B 5/0035 600/407 |
| --- | --- | --- | --- |
| 2013/0168532 A1* | 7/2013 | Schmid | G01N 29/045 250/205 |
| 2013/0276542 A1* | 10/2013 | Herzog | A61B 5/0073 73/655 |
| 2014/0046166 A1* | 2/2014 | Tokita | A61B 5/6844 600/407 |
| 2015/0051473 A1* | 2/2015 | Huang | A61B 5/0095 600/407 |
| 2015/0075287 A1* | 3/2015 | Herzog | A61B 8/4281 73/655 |
| 2015/0182123 A1* | 7/2015 | Sato | A61B 5/4312 600/407 |

(Continued)

*Primary Examiner* — Sean D Mattson
(74) *Attorney, Agent, or Firm* — Josef L. Hoffmann; The Small Patent Law Group LLC

(57) ABSTRACT

An optoacoustic probe for optoacoustic imaging of a volume, the optoacoustic probe having a distal end operable to contact the volume and a proximal end. The optoacoustic probe includes at least one primary light source and an auxiliary light source that is configured to generate auxiliary light carried through an optical window to a volume. A detection device is configured to detect signals generated from the auxiliary light or primary light reflecting from the volume or the optical window. A microcontroller including one or more processors is also provided, that receives the signals generated from the auxiliary light reflecting from the volume from the detection device, determines contact between the volume and the optoacoustic probe based on the auxiliary light reflecting from the volume, and prevents the at least one primary light source from generating light until the optoacoustic probe is contacting the volume.

19 Claims, 8 Drawing Sheets

(56) References Cited

U.S. PATENT DOCUMENTS

2015/0335252 A1* 11/2015 Hirota .................. A61B 5/7246
                                                        600/407
2017/0035348 A1*  2/2017 Bandic .................. A61B 5/442
2017/0108429 A1*  4/2017 Schmid ................ A61B 5/0035
2019/0200875 A1*  7/2019 Umezawa ............ A61B 5/0059
2019/0223733 A1*  7/2019 Irisawa ................. A61B 5/061

* cited by examiner

OPTOACOUSTIC PROBE

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present invention relates in general to the field of medical imaging, and in particular to a system relating to optoacoustic imaging.

BACKGROUND

Optoacoustic imaging systems visualize thin tissue slices noninvasively through skin at a tissue site. A tissue site may contain a variety of tissue structures that may include, for example, tumors, blood vessels, tissue layers, and components of blood. In optoacoustic imaging systems, light is used to deliver optical energy to a planer slice of the tissue site, which as a result of optical absorption with the tissue structures, produce acoustic waves. An image spatially representing the tissue site can be generated by performing image reconstruction on acoustic signals that return to an ultrasound transducer array. Because biological tissue scatters impinging optical energy in many directions the optical energy can be absorbed by tissue structures outside of a targeted region, which can generate acoustic return signals that interferes with the imaging of tissue structures within the targeted region.

Further, a laser light source typically provides the optical energy required to generate the acoustic waves. Consequently, during such operation, great care must be taken to ensure the emitted optical energy does not harm a patient and clinician, includes the eyes of the patient or clinician.

In order to prevent such harm, safety glasses are often worn by the clinician during such procedures. Additionally, probe holders are utilized that absorb or prevent the emission of the radiation, so that if a clinician forgets to turn off the probe, the radiation cannot harm any individuals in the environment. In other examples, the probe does not emit optical energy unless a foot actuator is utilized. Still, when the probe is removed from the holder, or when a clinical drops the probe while utilizing the foot actuator, potentially harmful optical energy may be emitted into the environment, increasing the chances of harm.

A need therefore exists for a more effective design for an OA probe that avoids potential safety hazards associated with the optical energy source.

BRIEF SUMMARY

New and useful systems, apparatuses, and methods for providing optoacoustic imaging are set forth in the appended claims. Illustrative embodiments are also provided to enable a person skilled in the art to make use the claimed subject matter.

Objectives, advantages, and a preferred mode of making and using the claimed subject matter may be understood best by reference to the accompanying drawings in conjunction with the following detailed description of illustrative embodiments.

In accordance with embodiments herein, an optoacoustic probe for optoacoustic imaging of a volume, the optoacoustic probe having a distal end operable to contact the volume and a proximal end. The optoacoustic probe includes at least one primary light source configured to generate light that is transmitted along a light path to generate optoacoustic return signals when the light reacts with the volume, and a transducer assembly including a transducer configured to receive the optoacoustic return signals and an acoustic lens provided over the transducer. An optical window is configured to carry light along the light path to the volume, and an auxiliary light source is configured to generate auxiliary light carried through the optical window to the volume. A detection device is configured to detect signals generated from the auxiliary light or primary light reflecting from the volume or the optical window. A microcontroller including one or more processors is also provided, and a memory is coupled to the one or more processors. The memory stores program instructions, and the program instructions are executable by the one or more processors to receive the signals generated from the auxiliary light reflecting from the volume from the detection device, determine contact between the volume and the optoacoustic probe based on the auxiliary light reflecting from the volume, and prevent the at least one primary light source from generating light until the optoacoustic probe is contacting the volume.

Optionally, the optoacoustic probe also includes a triggering system configured to actuate the primary light source and the auxiliary light source, and configured to prevent actuation of the primary light source before actuation of the auxiliary light source. In another aspect the optoacoustic probe also includes a foot actuator coupled to the triggering system, and responsive to actuation of the foot actuator, the triggering system actuates the auxiliary light source.

Optionally, the auxiliary light source is a light emitting diode and the primary light source is a laser. In another aspect, the detection device is disposed adjacent the optical window. In another aspect, the auxiliary light source is within a housing of the optoacoustic probe. Optionally, the auxiliary light source is within a laser head of the primary light source. In another aspect, the detecting device is at least one of a light sensor, thermopile, oxygen meter, piezoelectric sensor, spectrometer, digital camera, or charge couple device. In yet another aspect, signals generated from the auxiliary light reflecting from the volume are sound based signals.

In accordance with embodiments herein a method of triggering a primary light source of an optoacoustic probe is provide that includes actuating an auxiliary signal source to generate an auxiliary signal, and detecting the auxiliary signal generated from the auxiliary signal reflected from a volume. The method also includes determining when the optoacoustic probe contacts the volume based on the auxiliary signal reflected from the volume, and triggering the primary light source in response to determining the optoacoustic probe contacts the volume.

Optionally, the method also includes preventing the primary light source from actuating in response to determining the optoacoustic probe is not contacting the volume. In another aspect, the method includes preventing the primary light source from actuating in response to determining the optoacoustic probe is not contacting the volume includes ignoring a command to actuate the primary light source.

Optionally, the auxiliary signal is a light signal, and determining when the optoacoustic probe contacts the volume based on the auxiliary signal includes determining an increase of reflected light based on the auxiliary signal reflected from the volume. In another aspect, actuating the auxiliary signal source includes actuating a foot actuator coupled to the auxiliary signal source. Alternatively, the auxiliary signal is one of a sound signal, piezo based signal, or ultrasound signal.

In accordance with embodiments herein, a method of triggering a primary light source of an optoacoustic probe is provided that includes actuating an auxiliary light source to generate auxiliary light, and detecting signals generated from the auxiliary light reflecting from a volume. The method also includes determining an increase of reflected light based on the signals detected as the optoacoustic probe moves toward a volume, and determining when the optoacoustic probe contacts the volume based on the auxiliary light reflected from the volume. The method also includes varying an output of the primary light source in response to the increase of reflected light, and triggering the primary light source in response to determining the optoacoustic probe contacts the volume.

Optionally, the method also includes comparing the determined increase of reflected light based on the signals detected as the optoacoustic probe moves toward the volume to historical data that includes increases of reflected light as the optoacoustic probe moves toward the volume for different volumes. In another aspect, the method includes varying the output of the primary light source in response to the increase of reflected light includes increasing the output based on the comparison of the determined increase of reflected light and historical data.

In accordance with embodiments herein, an optoacoustic probe for optoacoustic imaging of a volume is provided. The optoacoustic probe has a distal end operable to contact the volume and a proximal end. The optoacoustic probe includes at least one primary light source configured to generate light that is transmitted along a light path to generate optoacoustic return signals when the light reflects from the volume, and a transducer assembly including a transducer configured to receive the optoacoustic return signals and an acoustic lens provided over the transducer. The optoacoustic probe also includes an optical window configured to carry light along the light path to the volume, an auxiliary light source configured to generate auxiliary light carried through the optical window to the volume, and a detection device configured to detect signals generated from the auxiliary light reflecting from the volume. The optoacoustic probe also includes a microcontroller including one or more processors, and a memory coupled to the one or more processors, wherein the memory stores program instructions, and wherein the program instructions are executable by the one or more processors to obtain the signals generated from the auxiliary light reflecting from the volume as the optoacoustic probe moves toward the volume, and determine a skin characteristic based on the signals generated from the auxiliary light reflecting from the volume as the optoacoustic probe move toward the volume. In response to determining the skin characteristic, the one or more processors are configured to vary an output of the at least one primary light source. Optionally, the skin characteristic is skin color.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION

Figure 1:
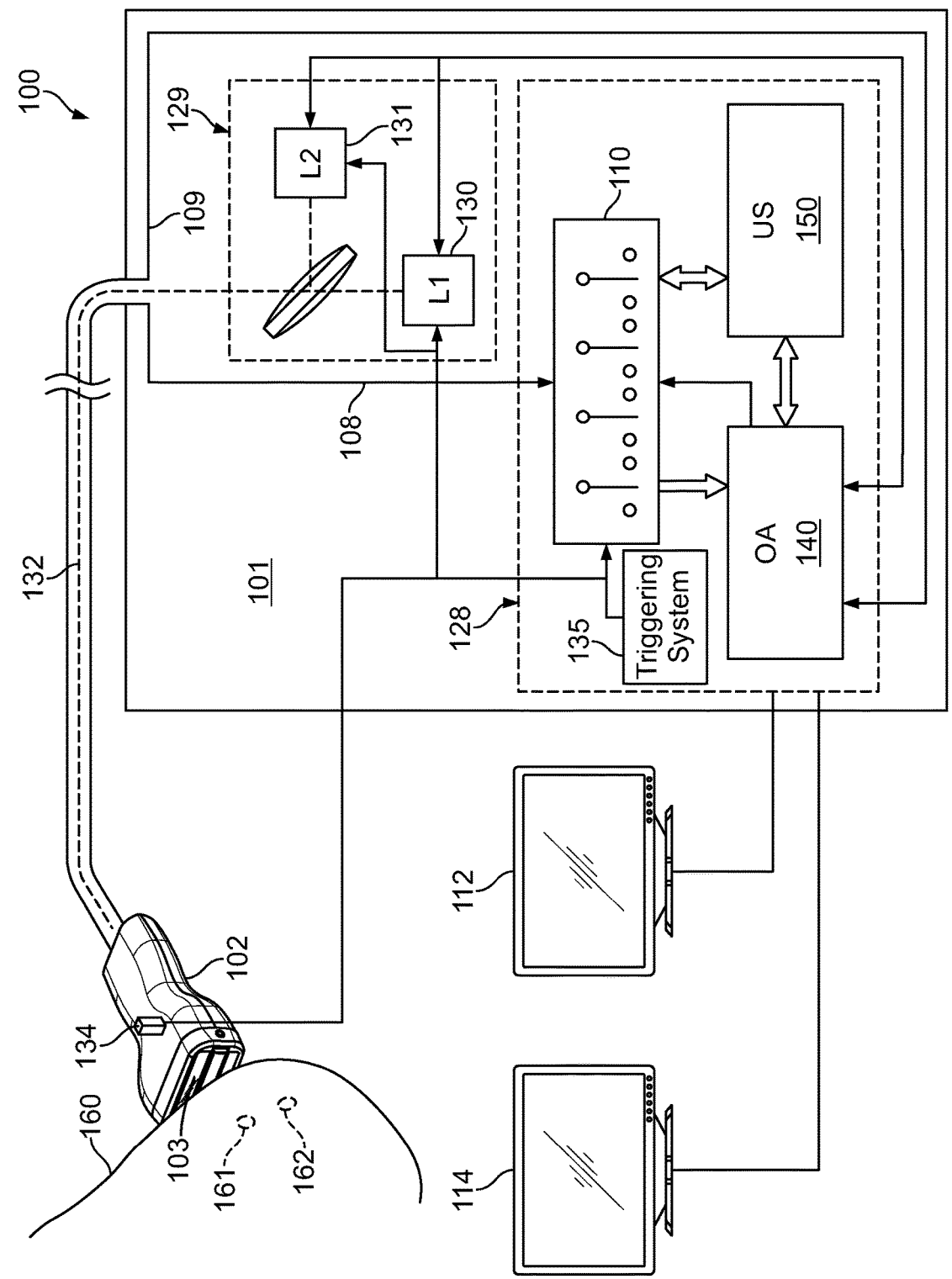
FIG. 1 shows a schematic block diagram illustrating an embodiment of a combined optoacoustic and ultrasound system that may be used as a platform for the methods and devices disclosed herein.

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The systems and methods are described below with reference to, among other things, block diagrams, operational illustrations and algorithms of methods and devices to provide optoacoustic imaging with out-of-plane artifact suppression. It is understood that each block of the block diagrams, operational illustrations and algorithms and combinations of blocks in the block diagrams, operational illustrations and algorithms, can be implemented by means of analog or digital hardware and computer program instructions.

These computer program instructions can be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

In some cases, frequency domain-based algorithms require zero or symmetric padding for performance. This padding is not essential to describe the embodiment of the algorithm, so it is sometimes omitted from the description of the processing steps. In some cases, where padded is disclosed in the steps, the algorithm may still be carried out without the padding. In some cases, padding is essential, however, and cannot be removed without corrupting the data.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Reference will now be made in more detail to various embodiments of the present invention, examples of which are illustrated in the accompanying figures. As will be apparent to one of skill in the art, the data structures and processing steps described herein may be implemented in a variety of other ways without departing from the spirit of the disclosure and scope of the invention herein and should not be construed as being limited to the embodiments set forth herein. Rather, these embodiments are provided so that this disclosure will be thorough and complete, and will fully convey the concept of the disclosure to those skilled in the art.

Embodiments herein may be implemented in connection with one or more of the systems and methods described in one or more of the following patents, publications and/or published applications, all of which are expressly incorporated herein by reference in their entireties:

U.S. Pat. No. 7,999,161, titled "Laser-Activated Nanothermolysis Of Cells" filed Jul. 23, 2007;

U.S. Pat. No. 9,289,191, titled "System and method for Acquiring Optoacoustic Data and Producing Parametric Maps Thereof", and filed Jun. 13, 2012;

U.S. Pat. No. 9,517,055, titled "System And Method For Acquiring Optoacoustic Data And Producing Parametric Maps Using Subband Acoustic Compensation" filed Nov. 25, 2013;

U.S. Pat. No. 9,724,072, titled "System And Method For Mixed Modality Acoustic Sampling" filed Dec. 13, 2013;

U.S. Pat. No. 9,456,805, titled "System And Method For Acquiring Optoacoustic Data And Producing Parametric Maps Using Interframe Persistent Artifact Removal" filed Dec. 19, 2013;

U.S. Publication 2016/0199037, titled "System And Method For Acquiring Optoacoustic Data And Producing Parametric Maps thereof" filed Mar. 22, 2016;

U.S. Publication 2017/0035388, titled "System And Method For Mixed Modality Acoustic Sampling" filed Oct. 18, 2016;

U.S. Pat. No. 9,792,686, titled "System And Method For Acquiring Optoacoustic Data And Producing Parametric Maps Using Subband Acoustic Compensation" filed Nov. 17, 2016;

U.S. Publication 2017/0296151, titled "System And Method For Mixed Modality Acoustic Sampling" filed Jun. 30, 2017;

U.S. Publication 2013/0109950, titled "Handheld Optoacoustic Probe" filed Nov. 2, 2011;

U.S. Publication 2016/0296121, titled "Handheld Optoacoustic Probe" filed May 2, 2016;

U.S. Pat. No. 8,686,335, titled "System And Method For Adjusting The Light Output Of An Optoacoustic Imaging System" filed Dec. 31, 2011;

U.S. Pat. No. 9,528,936, titled "System And Method For Adjusting The Light Output Of An Optoacoustic Imaging System" filed Mar. 31, 2014;

U.S. Publication 2017/0108429, titled "System And Method For Adjusting The Light Output Of An Optoacoustic Imaging System" filed Dec. 27, 2016;

U.S. Pat. No. 9,330,452, titled "Statistical Mapping In An Optoacoustic Imaging System" filed Mar. 11, 2013;

U.S. Pat. No. 9,836,838, titled "Statistical Mapping In An Optoacoustic Imaging System" filed May 3, 2016;

U.S. Publication 2018/0061050, titled "Statistical Mapping In An Optoacoustic Imaging System" filed Nov. 6, 2017;

U.S. Pat. No. 9,610,043, titled "System And Method For Producing Parametric Maps Of Optoacoustic Data" filed Jun. 13, 2012;

U.S. Publication 2017/0100040, titled "System And Method For Producing Parametric Maps Of Optoacoustic Data" filed Dec. 21, 2016;

U.S. Publication 2013/0338501, titled "System And Method For Storing Data Associated With The Operation Of A Dual Modality Optoacoustic/Ultrasound System" filed Jun. 13, 2012;

U.S. Publication 2013/0338475, titled "Optoacoustic Imaging System With Fiber Optic Cable" filed Jun. 13, 2012;

U.S. Publication 2014/0194723, titled "Multi-Layer Coating For Optoacoustic Probe" filed Jan. 13, 2014;

U.S. Publication 2017/0150890, titled "Optoacoustic Probe With Multi-Layer Coating" filed Jan. 31, 2017;

U.S. Pat. No. 9,615,750, titled "Methods And Compositions For Carrier Agents And Clearing Agents Used In Optoacoustic Imaging Systems" filed Jun. 14, 2012;

U.S. Publication 2013/0116538, titled "Optoacoustic Imaging Systems And Methods With Enhanced Safety" filed Oct. 19, 2012;

U.S. Publication 2015/0297090, titled "Optoacoustic Imaging Systems And Methods With Enhanced Safety" filed Jan. 23, 2015;

U.S. Publication 2013/0289381, titled "Dual Modality Imaging System For Coregistered Functional And Anatomical Mapping" filed Nov. 2, 2012;

U.S. Pat. No. 9,757,092, titled "Method For Dual Modality Optoacoustic Imaging" filed Nov. 2, 2012;

U.S. Publication 2014/0039293, titled "Optoacoustic Imaging System Having Handheld Probe Utilizing Optically Reflective Material" filed Jan. 22, 2013;

U.S. Publication 2017/0014101, titled "Dual Modality Imaging System For Coregistered Functional And Anatomical Mapping" filed Sep. 27, 2016;

U.S. Publication 2013/0303875, titled "System And Method For Dynamically Varying The Angle Of Light Transmission In An Optoacoustic Imaging System" filed Nov. 2, 2012;

U.S. Pat. No. 9,445,785, titled "System And Method For Normalizing Range In An Optoacoustic Imaging System" filed Dec. 21, 2012;

U.S. Pat. No. 9,282,899, titled "System And Method For Detecting Anomalous Channel In An Optoacoustic Imaging System" filed Dec. 21, 2012;

U.S. Publication 2014/0005544, titled "System And Method For Providing Selective Channel Sensitivity In An Optoacoustic Imaging System" filed Dec. 21, 2012;

U.S. Publication 2016/0317034, titled "System And Method For Providing Selective Channel Sensitivity In An Optoacoustic Imaging System" filed Jul. 11, 2016;

U.S. Pat. No. 9,445,786, titled "Interframe Energy Normalization In An Optoacoustic Imaging System" filed Jan. 22, 2013;

U.S. Publication 2017/0000354, titled "Interframe Energy Normalization In An Optoacoustic Imaging System" filed Sep. 19, 2016;

U.S. Publication 2014/0206978, titled "Probe With Optoacoustic Isolator" filed Jan. 22, 2013;

U.S. Pat. No. 9,743,839, titled "Playback Mode In An Optoacoustic Imaging System" filed Mar. 15, 2013;

U.S. Publication 2017/0332916, titled "Playback Mode In An Optoacoustic Imaging System" filed Jul. 27, 2017;

U.S. Pat. No. 9,398,893, titled "System And Method For Diagnostic Vector Classification Support" filed Mar. 11, 2014;

U.S. Pat. No. 10,026,170, titled "System And Method For Diagnostic Vector Classification Support" filed Jul. 19, 2016

U.S. application Ser. No. 16/022,138, titled "System And Method For Diagnostic Vector Classification Support" filed Jun. 28, 2018;

U.S. Pat. No. 9,730,587, titled "Diagnostic Simulator" filed Mar. 15, 2013;

U.S. Publication 2017/0332915, titled "Diagnostic Simulator" filed Jul. 27, 2017;

U.S. Pat. No. 8,823,928, titled "Light Output Calibration In An Optoacoustic System" filed Mar. 15, 2013;

U.S. Pat. No. 9,163,980, titled "Light Output Calibration In An Optoacoustic System" filed Jul. 11, 2014;

U.S. Pat. No. 9,814,394, titled "Noise Suppression In An Optoacoustic System" filed Mar. 15, 2013;

U.S. Publication 2018/0078144, titled "Noise Suppression In An Optoacoustic System" filed Nov. 13, 2017;

U.S. Pat. No. 9,733,119, titled "Optoacoustic Component Utilization Tracking" filed Mar. 15, 2013;

U.S. Publication 2017/0322071, titled "Optoacoustic Component Utilization Tracking" filed Jul. 27, 2017;

U.S. Publication 2015/0101411, titled "Systems And Methods For Component Separation In Medical Imaging" filed Oct. 13, 2014;

U.S. Publication 2015/0305628, titled "Probe Adapted To Control Blood Flow Through Vessels During Imaging And Method Of Use Of Same" filed Feb. 27, 2015

U.S. Publication 2016/0187481, titled "Opto-Acoustic Imaging System With Detection Of Relative Orientation Of Light Source And Acoustic Receiver Using Acoustic Waves" filed Oct. 30, 2015.

Turning to FIG. 1, generally, device 100 provides an optoacoustic system that may also be employed as multi-modality, combined optoacoustic and ultrasound system. In an embodiment, the device 100 includes a probe 102 connected via a light path 132 and an electrical path 108 to a system chassis 101. Within the system chassis 101 is housed a light subsystem 129 and a computing subsystem 128. The computing subsystem 128 includes one or more computing components for ultrasound control and analysis and optoacoustic control and analysis; these components may be separate, or integrated. In an embodiment, the computing subsystem comprises a relay system 110, a triggering system 135, an optoacoustic processing and overlay system 140 and an ultrasound instrument 150. In one embodiment, the triggering system 135 is configured to actuate and control operation of the primary light sources 130, 131 and an auxiliary signal source 134 that in one example is an auxiliary light source. In other examples, the auxiliary signal source may be a sound signal source, piezo based signal source, ultrasound signal source, or the like. The primary light sources 130, 131 are utilized in creating signals for imaging purposes, while the auxiliary signal source 134 is not utilized to create signals for imaging purposes. In an example, the triggering system 135 prevents actuation of the primary light sources 130, 131 before actuation of the auxiliary signal source 134. To this end, the triggering system 135 prevents actuation of the primary light sources 130, 131 until detected light from the auxiliary signal source 134 on a tissue indicates that the probe is contacting the volume 160.

Figure 4:
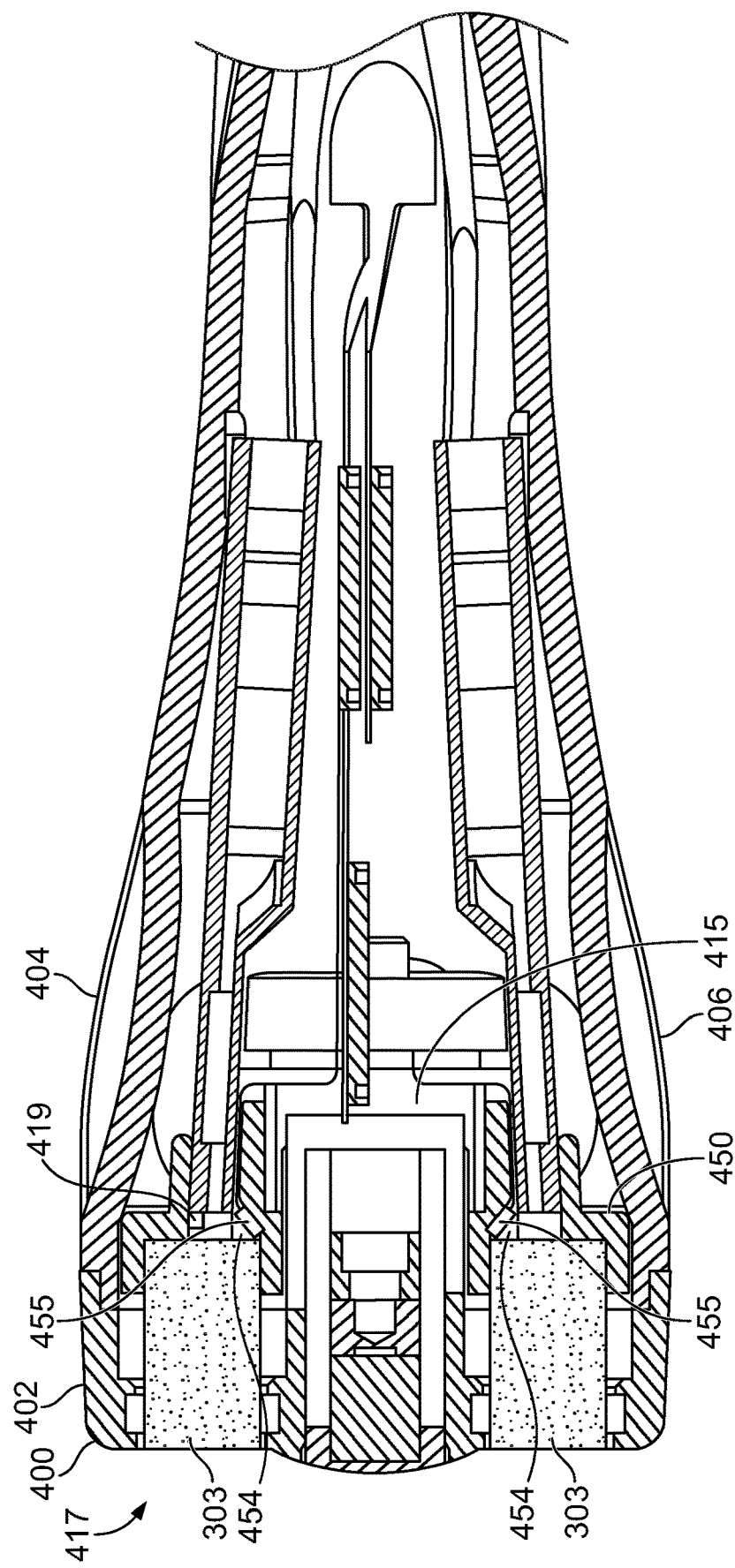
FIG. 4 shows a cross-sectional view of the probe shown in FIG. 3.

In an embodiment, the light subsystem 129 is capable of producing pulses of light of at least two different wavelengths. In an embodiment, the light subsystem 129 includes two separate primary light sources 130, 131 and an auxiliary signal source 134. In an embodiment the primary light sources 130, 131 are Nd:YAG and Alexandrite lasers. In example embodiments, the auxiliary signal source 134 may be light emitting diode, photodiode, low power laser, or the like. The output of the primary light sources 130, 131 of the light subsystem 129 is delivered to the probe 102 via the light path 132. In other example embodiment, the auxiliary signal source 134 is within the housing of the probe 102 and generates a light that exits the probe 102 through the one or more optical windows 103. Alternatively, the auxiliary signal source 134 is exterior to the probe housing. Specifically, whether within the probe housing or exterior to the probe housing, the auxiliary light source is positioned to emit light on organic tissue, phantom or other volume 160 to cause reflected light that may be received by one or more light detectors 455 (FIG. 4). In one example, the light detector 455 is in the distal end of the probe 102 and receives reflected light through the optical window 103.

One or more displays 112, 114, which may be touch screen displays, are provided for displaying images and all or portions of the device 100 user interface. One or more other user input devices (not shown) such as a keyboard, mouse and various other input devices (e.g., dials and switches) may be provided for receiving input from an operator.

Figure 2:
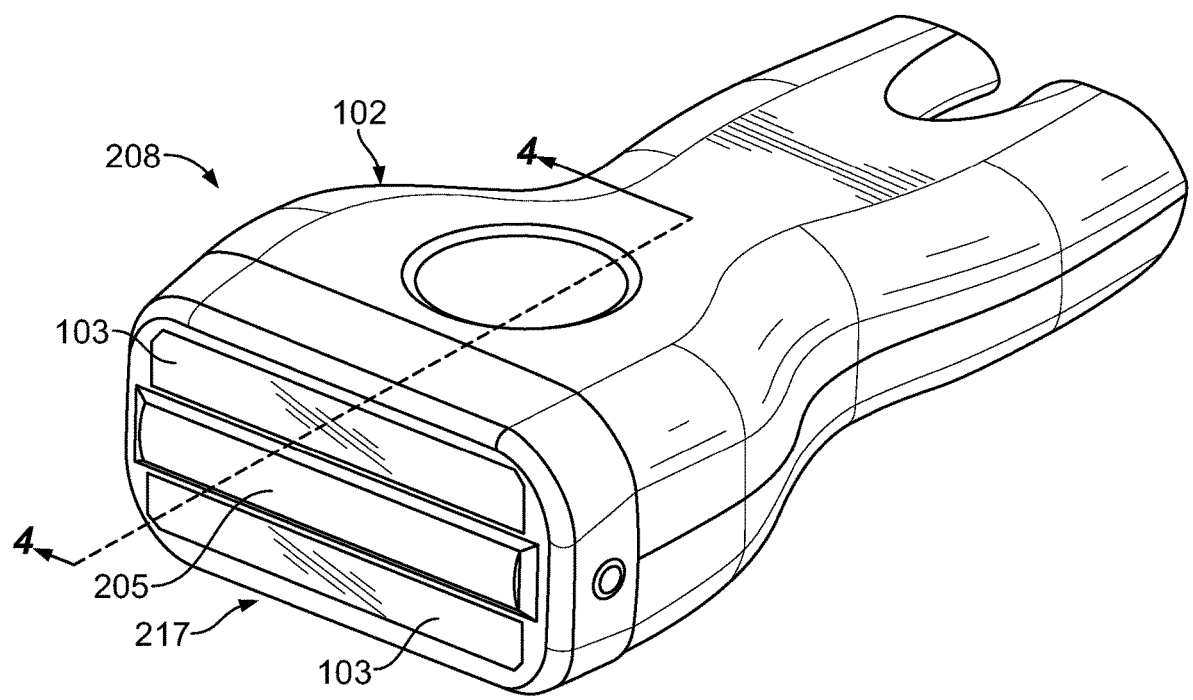
FIG. 2 shows a schematic orthogonal view of an embodiment of a probe that may be used in connection with the methods and other devices disclosed herein.

Turning now to FIG. 2, the probe 102 includes an ultrasound transducer covered by an acoustic lens 205. The probe 102 includes distal and proximal ends. A probe face 217 of the probe 102 is at the distal end 208. The probe 102 also includes one or more optical windows 103 through which the light carried on light path 132 can be transmitted to the surface of a volume 160, for example, a three-dimensional volume. Specifically, the probe 102 may be placed in close proximity with organic tissue, phantom or other volume 160 that may have one or more inhomogeneities 161, 162, such as e.g., a tumor, within. An ultrasound gel (not shown) or other material may be used to improve acoustic coupling between the probe 102 and the surface of the volume 160 and/or to improve optical energy transfer. The probe 102, when in proximity with the surface of the volume 160, can emit light from the auxiliary signal source 134 (FIG. 1) onto the surface of the volume 160 that is reflected and detected by one or more light detectors 455 (FIG. 4). The computing subsystem 128 may then make determination based on the reflected light regarding whether the probe 102 is contacting the volume 160 using methodologies described herein. Upon the determination of contact between the probe 102 and the volume, the computing subsystem 128 permits actuation of the primary light sources 130, 131 for generating otoacoustical feedback.

Figure 3:
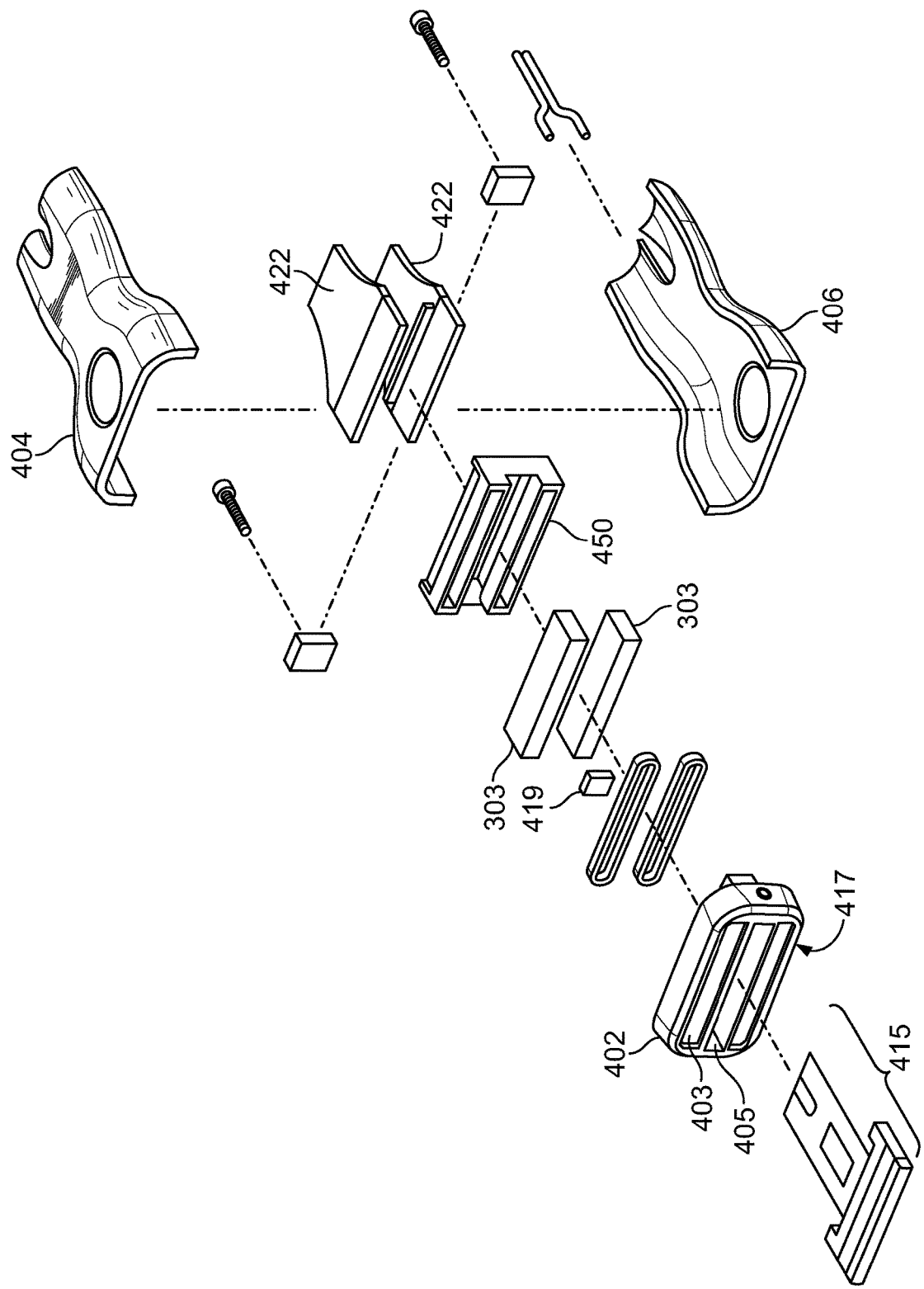
FIG. 3 shows an exploded view of an embodiment of the probe shown in FIG. 2.

FIGS. 3 and 4 show an exploded view and a cross-sectional view, respectively, of an embodiment of a probe that in one example is the probe 102 shown in FIGS. 1 and 2. In the embodiment of FIGS. 3 and 4, the probe 102 comprises a housing 400 including a distal portion 402 and first and second body portions 404, 406 which are shown separated to illustrate the components within the probe 102. The distal portion 402 includes a probe face 417. The distal portion 402 and the first and second body portions 404, 406 may be made from plastic or any other suitable material. Additionally or alternatively, in an embodiment the first and/or second body portions 404, 406 may include one or more regions that are characterized as acoustically reflective, for example, comprising an acoustically-reflective material. An auxiliary light source 419 is disposed within the housing 400. In one embodiment, the auxiliary light source 419 is disposed within the distal portion 402 of the housing 400 and positioned to direct light from within the housing, through an optical window 303 to be carried to a volume 160. The light then reflects off the volume, back through the optical window to create signals within the housing 400 that are detected by a detection device, such as light detector 455. The auxiliary light source 419 may be a light emitting diode, low level laser, or the like. The detection device may include a light sensor, thermopile, oxygen meter, piezoelectric sensor, spectrometer, digital camera, charge couple device, or the like. The detected signals may then be analyzed to determine when the probe contacts the volume.

Figure 5:
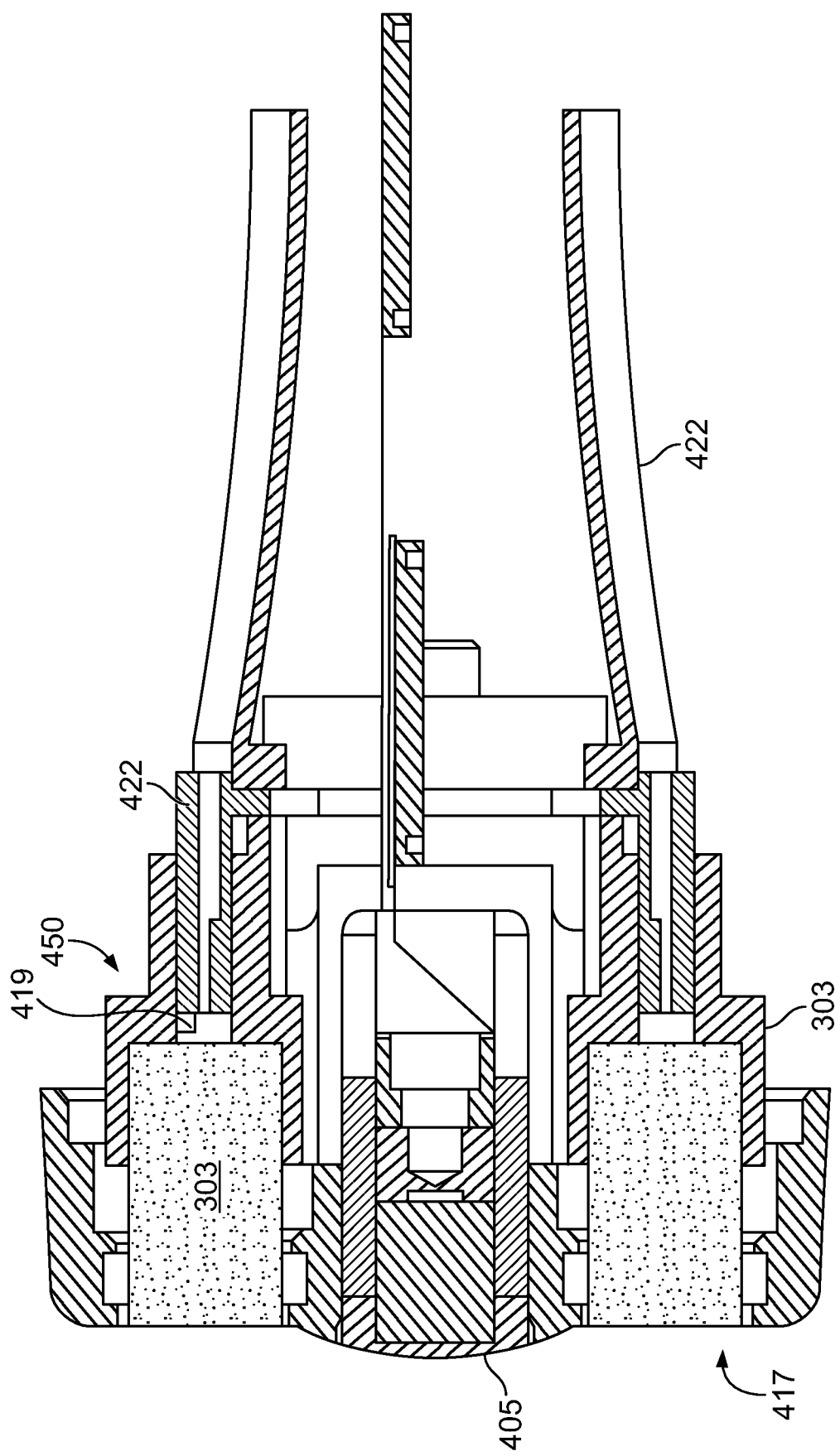
FIG. 5 shows a cross-sectional view of an embodiment of the distal housing portion shown in FIGS. 3 and 4.
Figure 6:
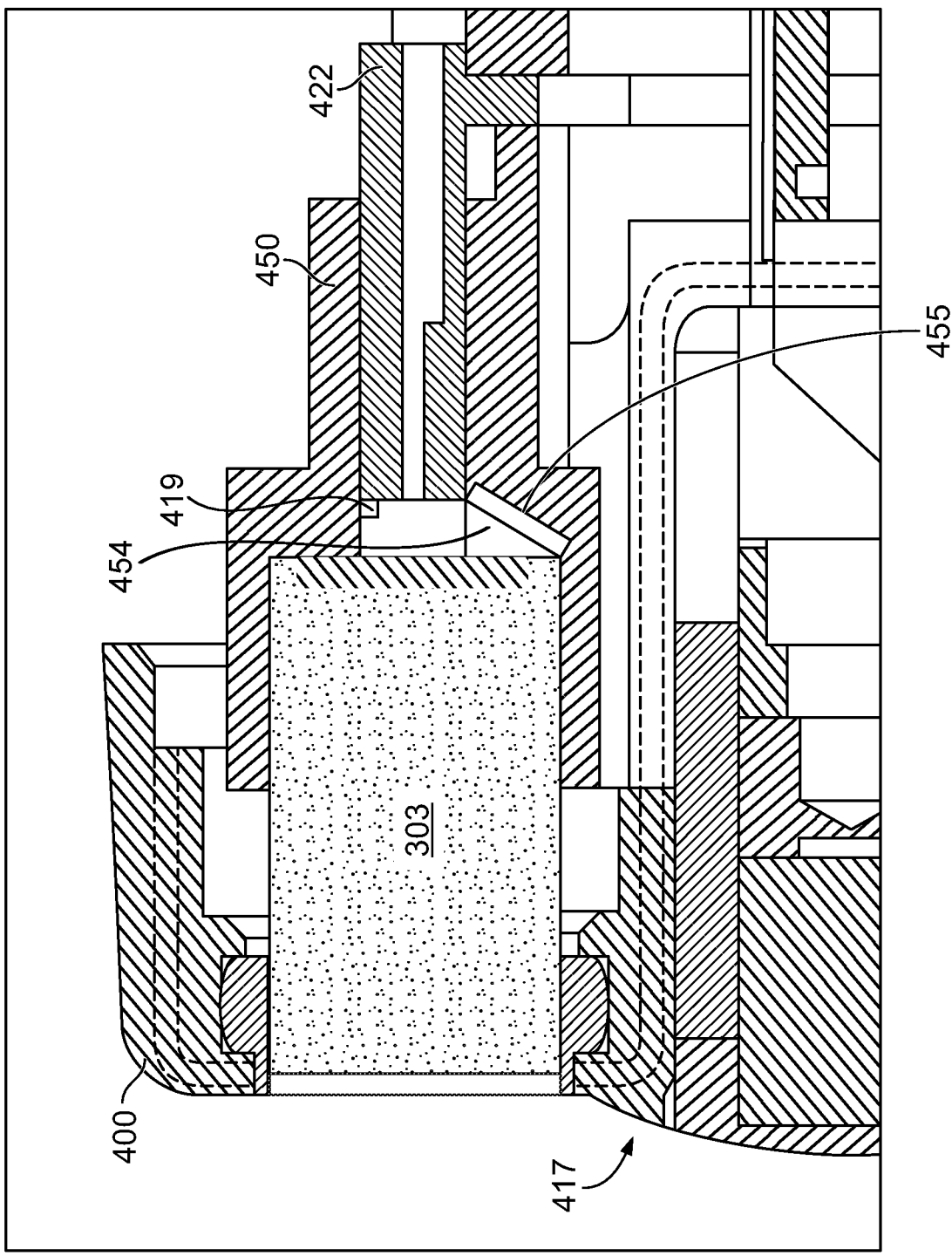
FIG. 6 shows an enlarged cross-sectional view of a distal portion of the probe housing.

Referring to FIGS. 5 and 6, the distal portion 402 of the housing is shown in a perspective view, in isolation. In the embodiment of FIG. 5, the distal portion 402 has a probe face 417 that includes an acoustic opening 405 into which the transducer assembly 415 is disposed and one or more optical openings 403 into which the optical windows 303 are disposed. The transducer assembly 415 and the optical windows 303 extending proximally from the probe face 417 (in the direction of arrow A). For example, in the embodiment of FIG. 5, the distal portion 402 includes two optical openings 403 into which two optical windows 303 are fitted and held on opposite sides of the transducer assembly 415. In accordance with embodiments herein, an optical barrier member is positioned to extend proximally from the probe face 417 between at least a portion of the optical window 303 and at least a portion of the transducer assembly 415. The optical barrier member may comprise one or more components as described herein.

The term "optical window," as used here, is not limited to an element having a particular structural, mechanical, or optical characteristic. Instead, the term is used to refer to an element that may or may not effect light passing therethrough, but will permit at least a substantial portion of the light incident on a surface of the optical window that is adjacent, or at least substantially proximate to the light path 132 to exit the probe 102 in a manner that is dependent on the properties of the optical window 303. In an embodiment, the optical window 303 is transparent or substantially transparent, permitting transmission of light, specifically, light emitted from the end of the light path 132, to the volume 160 when the distal end of the probe 102 is in contact with or close proximity to that volume 160.

In an embodiment the probe 102 further comprises an alignment bracket 450. The alignment bracket 450 may be generally configured to retain the optical windows 303 within the probe 102 such that the optical windows 303 are held in a desired orientation. In an embodiment, the alignment bracket 450 may also be configured to hold the optical windows 303 in a desired proximity to the light bar guide 422, particularly, from the ends of the optical fibers making up the light path 132.

In an embodiment, the alignment bracket 450 may also retain the optical windows 303 in a desired proximity to with respect to the transducer assembly 415. In an embodiment, when assembled, the alignment bracket 450 fits within the distal portion 402 such that the transducer assembly 415 is spaced from the alignment bracket by gaps 454 on either side of the transducer assembly. In an embodiment, the probe 102 includes a light detector 455 disposed within each of the gaps 454. In various embodiments, the light detectors 455 may be effective to take measurements from which output energy can be estimated or deduced. In an embodiment, the light detector 455 will measure reflected energy such as energy reflected internally within the probe 102. In an embodiment, the light detector 455 will measure scattered energy. The measurement of the light detector 455 can be transmitted to the system chassis 101 via control path(s) 109, where it can be analyzed to deduce or estimate the light output of the probe 102. In an embodiment, control functionality in the system chassis 101 can control or regulate the light output of the light subsystem 129, and thus the light output of the probe 102 based on a measurement made by the light detector 455. In an embodiment, control functionality in the system chassis 101 can control or regulate the gain in the transducer receivers to compensate for variation of the light output of the probe 102 based on a measurement made by the light detector 455. In an embodiment, the computing subsystem 128 can trigger differing activity from light subsystem 129 over a control signal line based on a measurement made by the light detector 455.

Additionally or alternatively, the light detector 455 may also measure light reflected from the tissue, for example, which can be used to determine amount of light entering tissue so that the system can adjust the light energy so as to maintain consistent light penetration across the different skin types. In an embodiment, a measurement made by the light detector 455 can be used to control for variations in the electrical system or the power to the device 100. Similarly, in an embodiment, a measurement made by the light detector 455 can be used to control for variations in the light path 132 or other optical elements of the device 100. In an embodiment, the light detector 455 can be used to cause the fluence of light output by the probe 102 to remain close to, but below, safe limits by accommodating for variations in electrical or optical characteristics that might otherwise cause the fluence of light output by the probe 102 to exceed or fall far below the safe limit. In another example, the light detector 455 may measure light reflected from the tissue from an auxiliary signal source 134, wherein a computing subsystem 128 prevents actuation of primary light sources 130, 131 until the probe 102 contacts the tissue. Based on the determination that the probe 102 is contacting the tissue, the primary light sources are then able to actuate and emit light. Consequently, a safety feature is provided.

In an embodiment, sensors, for example, photodetectors such as light detectors 455, can be placed within or in close proximity to the light subsystem 129 and within or in close proximity to the probe 102. In each case, the sensors would take a measurement during the illumination of a light sources 130, 131 which can be used to infer total and peak power. For this purpose, one or more light detectors 455 can be placed inside the probe 102 to measure reflection from the optical window. Similarly, one or more light detectors 455 can be placed within the light subsystem 129 to measure light reflected therein. Deviation over time in the measurements inferred between the two sensor locations may be indicative of anomalies in the light path 132.

Discussing now an embodiment of the system having light detector 455 such as photodetectors within or in close proximity to the probe 102. In an embodiment, one or more light detectors 455 may be placed within the probe, in the gap 454 to measure reflection from the optical window. Alternatively, or additionally, in an embodiment, one or more light detectors 455 may be provided light directly from a component of the light path 132, such as from one or a small plurality of the optical fibers that make up the light path 132. Alternatively, or additionally, in an embodiment, one or more light detector 455 may be provided light by another path provided within the probe, including light from an auxiliary signal source 134. Thus, for example, one or more light detectors 455 could be located within the end of the probe opposite the optical windows 303, and an auxiliary light path can be reflected from a tissue or otherwise, to the one or more light detectors 455.

Alternatively, or additionally, in an embodiment, one or more light detectors 455 may be arranged to detect light originating from the auxiliary light source 419 and corresponding auxiliary light path, after it has been reflected from the surface of volume 160. Using information from sensors arranged to detect light reflected from the surface of volume 160, can provide information related to the distance, or proximity of the probe 102 in relation to the tissue. In one embodiment, this includes determinations of when the probe 102 contacts the tissue.

In an embodiment, one or more light detectors 455 within, or in close proximity to, the probe 102 can be used as part of a system and method for safely starting the device 100 and then bringing the laser to its safe power potential. In particular, an auxiliary signal source 134 may be utilized and emitted onto the tissue to determine when the probe 102 contacts the tissue. In one embodiment, the computing subsystem prevents actuation of the primary light sources 130, 131 until the one or more light detectors 455 receive reflected light from the tissue that indicates the probe 102 is in contact with the tissue as is described in methods herein. This includes preventing actuation of the primary light sources, even when a secondary actuation device such as a foot pedal is actuated. This prevents undesired emissions of potentially harmful laser light from the primary light sources 130, 131.

Figure 7:
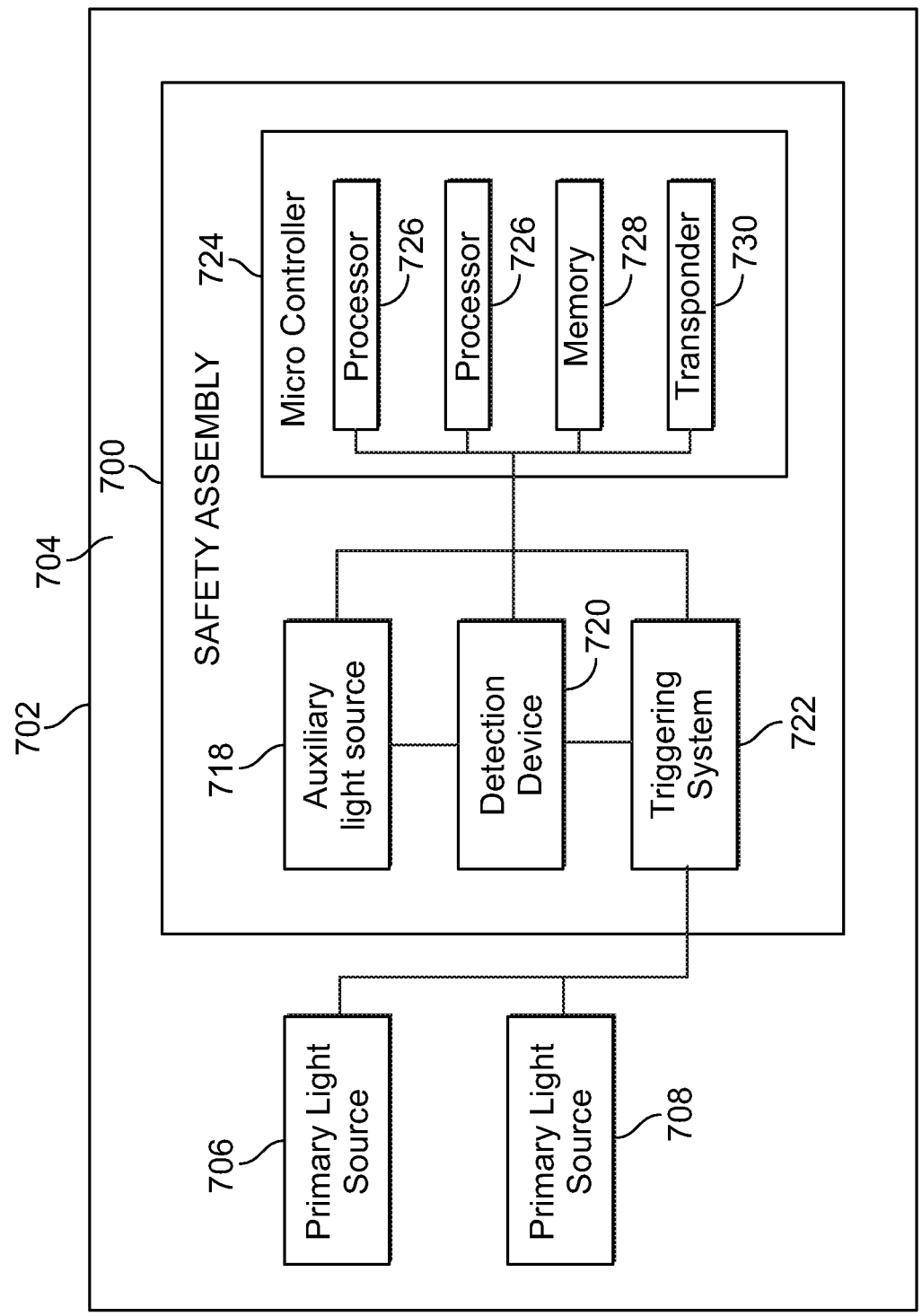
FIG. 7 shows a schematic block diagram of an embodiment of a combined optoacoustic and ultrasound system that may be used as a platform for the methods and devices disclosed herein.

FIG. 7 illustrates a block diagram of a safety assembly 700 for an optoacoustic probe 702. In one example the probe 702 is the probe 102. The probe 702 includes a housing 704 that receives a first primary light source 706 and a second primary light source 708 that each provide light along a light path through the housing 704. In one example the housing 704 is housing 400 described herein, while the first primary light source 706 and second primary light source 708 are primary light sources 130 and 131 also described herein. In one example the first primary light source 706 and second primary light source 708 are both laser light sources as described herein. The light path is disposed though the interior of the housing 704 and projects out of the housing 704 through an optical window to reflect off a volume of a patient (not shown). The volume may include tissue of a patient such as the breast or prostrate, a phantom, or the like. The probe 702 also includes a transducer assembly, including a transducer that is configured to receive an optoacoustic return signal from light, or optical energy reflecting off the volume. In one example an acoustic lens is provided over the transducer.

The safety assembly 700 includes an auxiliary light source 718 and a detection device 720 that is coupled to a triggering system 722. A microcontroller 724 is operably connected to the detection device 720 for receiving signals from the detection device 720 and transmitting the received signals to remote devices (not shown). The triggering system 722 specifically is operably coupled to the first and second primary light sources 706, 708, and to the auxiliary light source 718 such that the first and second primary light sources 706, 708, and auxiliary light source 718 are prevented from actuation, or emitting optical energy, including light, until a predetermined event or condition occurs. Such predetermined event or condition may include manual actuation through a button, foot actuator, or the like. Alternatively, such predetermined event or condition may include a determination that the probe 702 is engaging the volume, or is at a predetermined threshold distance from the volume, based on signals generated from the reflection of light from the auxiliary light source from the volume.

The auxiliary light source 718 may include a light emitting diode, including a light emitting diode of a specific wavelength range. Alternatively, the auxiliary light source 718 may be a photodiode, low powered laser, or the like that emits light at an energy level and wavelength that is not harmful to clinician or patient, but able to form signals when reflected off a volume that can be detected by the detection device. The auxiliary light source 718 may be located within the housing 704, secured to the housing 704, remote to the housing 704, or the like. Specifically, the auxiliary light source 718 is positioned in a location that is able to emit light on the volume to result in the reflection of the light off the volume, or tissue, through the optical window, and to the detector device, such that the change in reflection detected by the detection device 720 can indicate contact between the probe 702 and the volume. In one example the auxiliary light source 718 is disposed within a distal end of the housing within an airgap disposed therein. In one example the airgap is airgap 454 described herein. Alternatively, the auxiliary light source 718 is located exterior or remote from the probe housing 704. In another example the plural auxiliary light sources are provided, each capable of emitting light onto the volume to be reflected and detected by the detection device 720. The microcontroller 724 may then selectively actuate the different auxiliary light sources as required to ensure regardless of the angle of the probe 702 compared to the volume, or the color of the volume, sufficient light is presented to determine the location of the probe 702 in relation to the volume.

In example embodiments, the auxiliary light source 718 remains constantly in operation emitting light. In another example, a triggering device such as a button, touch screen, switch, foot pedal, or the like is utilized by the triggering system 722 to trigger, or actuate the auxiliary light source 718 with use of the probe 702 is desired. While the auxiliary light source 718 emits light, the triggering system 722 prevents the first and second primary light sources 706 and 708 from emitting optical energy. Upon and in response to the determination by the microcontroller 724 that the probe 702 is contacting the volume, the triggering system 722 then actuates the first and second primary light sources 706 and 708 to permit the emission of optical energy from the first and second primary light sources 706 and 708. In this manner, the triggering system 722 prevents potential harmful optical radiation from being emitted by or through the probe 702 until the probe 702 is contacting the volume. Therefore, safety in use is presented accordingly.

The detection device 720 is positioned to receive reflected light reflected from both an optical window and the volume or tissue. In one example the detection device is the light detector 455 described herein and is located within the probe housing 704. In one example the detection device 720 is located within the airgap 454 described herein. While the detection device 720 may be a light detector, in other examples the detection device may be a thermopile, oxygen meter, piezoelectric sensor, spectrometer, digital camera, charge couple device, or the like. In particular, while the auxiliary light reflecting off the volume results in reflected light waves, in addition, such reflected light waves also result in changes in temperature, changes in oxygen levels at the distal end of the probe 702, changes in pressure, or the like, and such signals may be similarly detected by the detection device 720 to determine the location of the probe in proximity to the volume. This includes signals sufficient to determine when the probe is contacting the volume. In yet another example, more than one detection devices are provided to increase the number of signals received by the safety assembly 700. Regardless of the type and amount of detection devices 720, in each example, safety assembly 700 receives feedback signals resulting from the reflection of the auxiliary light against the volume is acquired. These feedback signals may then by utilized in association with a mathematical determination including an algorithm, mean, average, or the like, compared to historical data within a look up table, or the like, to determine the location of the probe 702 in relation to the volume, including when the probe 702 contacts the volume. Historical data may include tables, graphs, charts, feedback signals of other patients, averaged feedback signals of other patients, median feedback signals of other patients, and the like.

The triggering system 722 is coupled to the microcontroller 724 in order to selectively actuate the first and second primary light sources 706 and 708 along with the auxiliary light source 718 based on predetermined events or conditions as discussed above. In an example, when the auxiliary light source 718 is within the probe housing 704 and directs the auxiliary light through the optical window 712, when no volume is presented, the detection device 720 detects the reflection of the auxiliary light from the optical window 712. In this manner a low level of optical energy, or signals are detected. As the probe moves closer to the volume, the amount of light reflecting off the volume or tissue continues to increase, causing increased signals detected at the detection device, with a maximum reflection occurring when the probe engages the volume. This increase to a maximum reflection detected, coupled with the steady reflection after contact, indicates contact between the probe 702 and the volume. Such determination may be made through use of a mathematical determination, a look up table with historical data, or the like. Once the probe 702 is determined to be contacting the volume, the triggering system 722 either allows actuation of the first and second primary light sources 706 and 708 through a triggering device, such as a foot pedal, or automatically actuates the first or second primary light sources 706 and 708. In such a manner, accidental triggering is reduced.

Alternatively, in a triggering system 722 when the auxiliary light source 718 is exterior of the probe 702, the detection device 720 does not detect any reflected light until the volume comes into proximity with the probe 702. As the probe 702 moves closer to the volume, the reflection of such light will increase until the volume or tissue no longer receives the light based on the angle of the auxiliary light source 718. Still, this pattern of increased reflection followed by an abrupt decline of reflection may be determined to represent the contacting of the probe of the volume. Such determination may be made by a mathematical determination, comparison of detected signal readings to historical data in a look up table, or the like. Once the condition of probe contact is met, the triggering system 722 either allows actuation of the first and second primary light sources 706 and 708 through a triggering device, or automatically actuates the first or second primary light sources 706 and 708. In such a manner, accidental triggering is reduced.

The microcontroller 724 in one example is part of the computer subsystem 128 described herein. In another example, the microcontroller 724 is within the housing 704, whereas in other examples the microcontroller 724 is remote from the housing and the detection device 720 communicates wirelessly with the microcontroller 724. The microcontroller 724 includes one or more processors 726 for making determinations, a memory 728 for storing instructions and historical data, including look up tables, and a transponder 730 for receiving and transmitting communication signals to and from the probe 702. In this manner, the one or more processors are configured to execute instructions to actuate the auxiliary light source, receive data signals from the detection device 720 related to reflected auxiliary light from the volume, determine the location of the probe 702 relative to the volume based on received data signals, prevent actuation of the first and/or second primary light sources until a predetermined condition, such as contacting of the probe 702 to the volume occurs, receive transmissions or commands to actuate the first and/or second primary light source, ignore commands to actuate the first and/or second primary light sources when a predetermined condition is not presented, automatically actuate the first and/or second primary light sources 706, 708 when a predetermined condition is determined, or the like. By utilizing an auxiliary light source 718, determinations may be made related to the position or location of the probe 702 utilizing non-harmful light to ensure that the first and/or second primary light sources 706, 708 only emit optical energy when desired for taking readings related to the volume. In all, the emission of potentially harmful optical energy into the clinical environment is reduced and overall safety increased.

Figure 8:
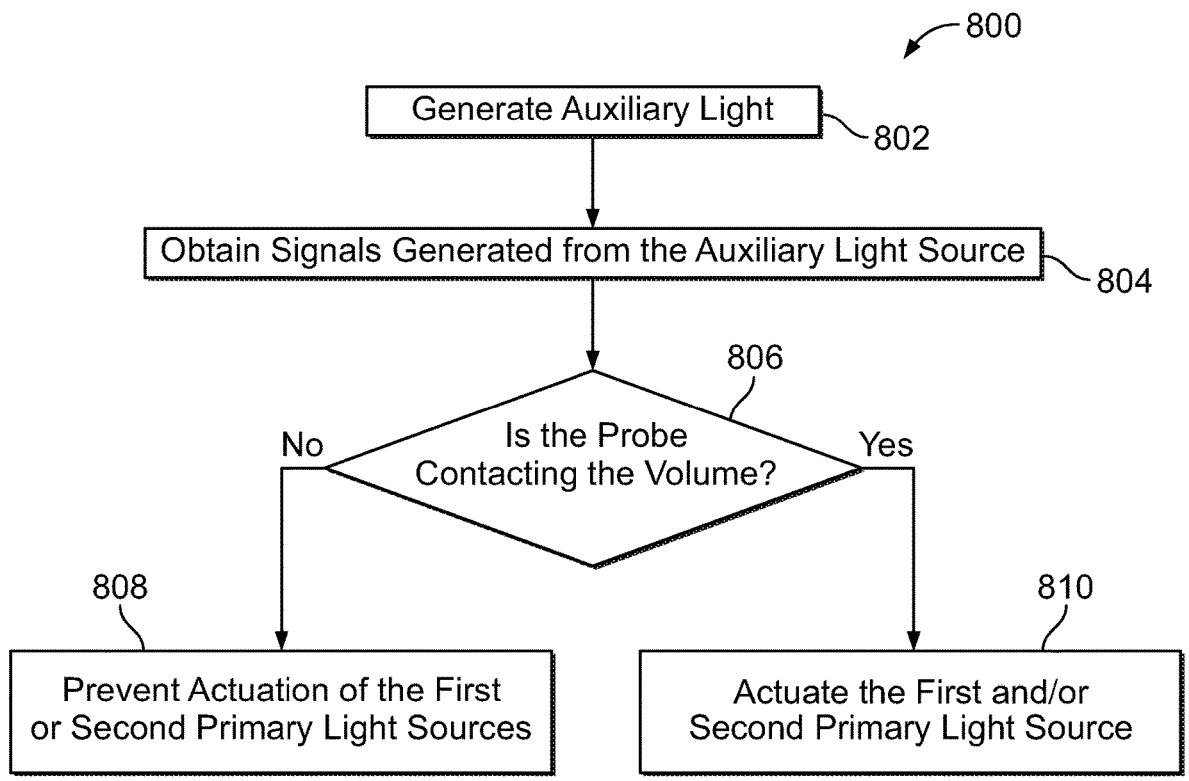
FIG. 8 shows a block flow diagram of a method of triggering a primary light source of an optoacoustic probe for the devices disclosed herein.

FIG. 8 illustrates a method 800 of triggering a primary light source of an optoacoustic probe. At 802, an auxiliary light source is actuated to generate auxiliary light. In one example the auxiliary light source is auxiliary light source 718 of FIG. 7. To this end, the auxiliary light source may be a light emitting diode, including a light emitting diode of a specific wavelength range, a photodiode, low powered laser, or the like, each that emits light at an energy level and wavelength that is not harmful to clinician or patient, but able to form signals when reflected off a volume that can be detected by the detection device. The auxiliary light source in one example is actuated as a result of a trigger device being manually actuated by a clinician. Such trigger devices may include buttons, touch screens, foot pedals, or the like. Alternatively, the auxiliary light source is automatically actuated by one or more processors as a result of a preexisting condition or event. In one example, when the probe is removed from a probe holder, the one or more processors automatically actuate the auxiliary light source to emit light. In yet another example, when the probe is within a probe holder, a circuit resulting in actuation of the auxiliary light source is broken as a result of the design of the probe holder, resulting in no light being emitted by the auxiliary light source, then, when removed from the probe holder, the circuit is complete, resulting in actuation of the auxiliary light source. Alternatively, the one or more processors may include a timer, wherein the auxiliary light source emits light during a predetermined interval when a medical procedure is to be undertaken. Actuation may be as a result of manual actuation, one or more processors, a triggering system, or the like.

At 804, a detection device obtains signals generated from the auxiliary light source. In an example, the detection device is the detection device 720 of FIG. 7. To this end, the detection device may be one of a thermopile, oxygen meter, piezoelectric sensor, spectrometer, digital camera, charge couple device, or the like. In one example, the signals generated from the auxiliary light source include a direct measurement of the auxiliary light from the auxiliary light source. Signals also include from auxiliary light that is reflected off of an optical window at a distal end of the probe. The signals may also include signals reflected off of a volume exterior to the probe. Signals can also include sound based signals, pressure based signals, oxygenation based signals, or the like that are generated as a result of the auxiliary light reflecting off of a volume and back into the probe. Each of these signals may be obtained such that one or more processors may make determinations related to the amount of auxiliary light exiting the optical window compared to auxiliary light reflected off the optical window, or a volume. Specifically, in an example, when no volume is presented, 10% of the light emitted against the window may be detected by the detection device, whereas, as the probe first detects the volume, 20% of the light emitted against the window may be detected. One or more processors may determine that a 10% increase in signals has occurred. Similarly, as the probe continues to move toward the volume, the number of reflected signals detected and obtained by the detection device continues to increase until contact with the volume. In one example 60% of the emitted light is detected from the signals at contact. At the point of contact, the number of signals detected remains relatively unchanged and at the constant 60% level. The one or more processors can determine that the probe is contacting the volume as a result of the 60% level being detected, or because the 60% level remains constant for a predetermined period.

At 806, the one or more processors determine that the probe is contacting the volume. As discussed in the previous paragraph, such determination may be made as a result of the change in reflected signals received by the detection device as the probe moves toward and contacts the volume. Specifically, the one or more processors may utilize a mathematical determination to make such a determination. Alternatively, a threshold value may be utilized to determine that probe is contacting the volume. In one example, the threshold value is 50% such than when more than 50% of the emitted light is detected as reflected by the detection device, the probe is considered to be contacting the volume. Such determination may be as an if, then statement of software. In yet another example, a lookup table within a memory of a microcontroller is accessed and when the reflected light is in a range between 50%-100%, the determination is made the probe is contacting the volume. When describing the one or more processors as making a determination that the probe is contacting the volume, in some examples, while the detected signals will indicate that the probe is contacting the volume, in other examples, the probe may not be contacting the volume. Still, in such examples, the probe will be in such close proximity to the volume, that even will not be contacting the volume, the safety improvements are still presented.

In yet another example, when the pigment of skin reflecting light does not reflect at a rate similar to another pigment of skin, such determination may still be made. Specifically, for darker tones of skin, reflection of light will be reduced, causing use of a threshold value to determine when the probe is contacting the volume to potentially cause inaccuracies. Still, the pattern of the increase of reflected light detected by the detection device may be used. Specifically, as the probe moves closer to the volume, regardless of pigment tone, the detection device will increase reflectance, just not as a great of rate as when a different pigment tone is provided. Still, the increase in reflectance signal is still indicative of the probe moving toward the volume, and such change in reflectance may be utilized to determine when the probe contacts the volume. In all, characteristics of interest of the signals, including percentage of reflected light detected, change in reflected light detected over time, or the like is utilized to determine when the probe contacts the volume.

If at 806, the probe is determined to not be contacting the volume, then flow moves to 808, and one or more processors prevent actuation of the first or second primary light sources. Flow then moves back to 806 to continuously determine if the probe is contacting the volume. In an example of when the one or more processors prevent actuation, if the probe is moving toward the volume, but the signals resulting from the reflection of light detected by the detection device do not result in a determination that the probe is contacting the volume, the one or more processors prevent actuation of the first and second primary light sources. Consequently, in an example when a clinician is commanding the first and/or second primary light sources to emit light, such as when a clinician is manually pressing a button, is using a foot pedal actuator, or the like, and the clinician drops the probe, causing it to no longer be contacting the volume, when the one or more processors determine contact does not exist between the probe and volume, the one or more processors prevent additional actuation of the first and/or second primary light sources even though the clinician continues manually commanding actuation. In the foot pedal example, if the probe is dropped by the clinician, even though the clinician keeps their foot on the foot pedal, in response to determining the probe is no longer contacting the volume, the one or more processors ignore the command signal to cease emission of optical energy by the first and/or second primary light sources. As a result, the one or more processors prevent potentially harmful optical energy from being emitted into the environment when the probe is no longer contacting the volume.

If at 806 the probe is determined to be contacting the volume, then optionally, flow moves to 810, and a triggering system automatically actuates, or triggers, the first and/or second primary light source. After the first and/or second primary light source is actuated, flow moves back to the determination at 806 as the one or more processors, continuously determine if the probe is contacting the volume. When the probe is contacting the volume, the first and second primary light sources are able to generate or emit light in response to the probe contacting the volume.

Similarly, in another example, if at 806, the probe is determined to be contacting the volume, then at 810 the triggering system allows the first and/or second primary light sources to be triggered or actuated upon command of a clinician. In one example, the command is provided manually through compressing a button, touching a screen, compressing a foot pedal or the like. In this manner, the clinician still has manual control over the triggering of the first and/or second primary light sources, providing additional timing control for the clinician related to taking measurements and obtaining images. In sum, improved control and safety are both provided by utilizing the probe and methodology provided.

Figure 9:
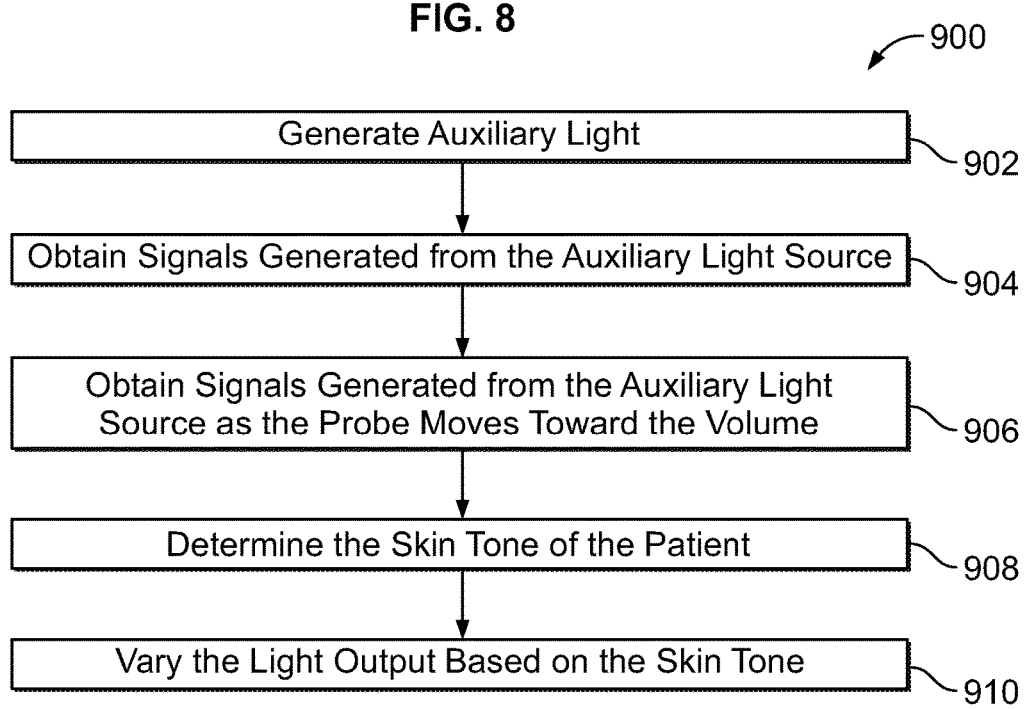
FIG. 9 shows a block flow diagram of a method of triggering a primary light source of an optoacoustic probe for the devices disclosed herein While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

FIG. 9 illustrates a method 900 of varying light source power for an optoacoustic probe. Specifically, when utilizing an optoacoustic probe consideration must be made in relation to the tone of skin, or pigment color of the patient. In particular, skin color has a direct effect on the amount of light may be reflected of the surface of the skin for providing signals that can be utilized by the transducers of an optoacoustic probe to provide imaging. In an embodiment when an auxiliary light is utilized, such as the auxiliary light of FIG. 7, by evaluating the change in signals detected by a detection device based on the reflection of the auxiliary light on a volume as the probe moves toward the volume and then contacts the volume, the skin color or tone of a patient may be determined. Then based on this skin color, one or more processors may vary the power of the optical energy emitted by the first and/or second primary light source to increase or decrease the number of signals resulting from the reflection of the light in a light path from the first and/or second primary light sources. Consequently, an improved image results.

At 902, the auxiliary light source is actuated to generate auxiliary light. In one example the auxiliary light source is auxiliary light source 718 of FIG. 7. To this end, the auxiliary light source may be a light emitting diode, including a light emitting diode of a specific wavelength range, a photodiode, low powered laser, or the like, each that emits light at an energy level and wavelength that is not harmful to clinician or patient, but able to form signals when reflected off a volume that can be detected by the detection device. The auxiliary light source is one example is actuated as a result of a trigger device being manually actuated by a clinician. Such trigger devices may include buttons, touch screens, foot pedals, or the like. Alternatively, the auxiliary light source is automatically actuated by one or more processors as a result of a preexisting condition or event. In one example, when the probe is removed from a probe holder, the one or more processors automatically actuate the auxiliary light source to emit light. In yet another example, when the probe is within a probe holder, a circuit resulting in actuation of the auxiliary light source is broken as a result of the design of the probe holder, resulting in no light being emitted by the auxiliary light source, then, when removed from the probe holder, the circuit is complete, resulting in actuation of the auxiliary light source. Alternatively, the one or more processors may include a timer, wherein the auxiliary light source emits light during a predetermined interval with a medical procedure is to be undertaken. Actuation may be as a result of manual actuation, one or more processors, a triggering system, or the like.

At 904, a detection device begins obtaining signals generated from the auxiliary light source. In an example, the detection device is the detection device 720 of FIG. 7. To this end, the detection device may be one of a thermopile, oxygen meter, piezoelectric sensor, spectrometer, digital camera, charge couple device, or the like. In one example, the signals generated from the auxiliary light source include a direct measurement of the auxiliary light from the auxiliary light source. Signals also include from auxiliary light that is reflected off of an optical window at a distal end of the probe. The signals may also include signals reflected off of a volume exterior to the probe. Signals can also include sound based signals, pressure based signals, oxygenation based signals, or the like that are generated as a result of the auxiliary light reflecting off of a volume and back into the probe. Each of these signals may be obtained such that one or more processors may make determinations related to the amount of auxiliary light exiting the optical window compared to auxiliary light reflected off the optical window, or a volume.

At 906, the detection device continuously obtains signals generated from the auxiliary light reflecting from a volume as the probe moves toward the volume. Specifically, as the probe moves toward the volume, the amount of reflected light detected by the detection device increases until the probe contacts the volume.

At 908, the one or more processer determines the skin tone of the patient based on the continuously obtained signals generated as the probe moves toward the volume. In particular, as the probe moves toward the volume, the rate of detected signals from the reflection of the auxiliary light increases as a resulted of the reduction in scattering of light that occurs as the distance between the probe and volume decreases. Still, the amount of increase is directly proportional to the skin color of the patient, because individuals with lighter skin tone absorb less light, and reflect light at a greater rate than darker skin tones. In this manner the amplitude, or rate at which the increase in signals received based on the reflected light is directly proportional to skin color.

At 910, in responses to determining the skin tone, the one or more processors vary the output of the first and/or primary light sources to increase or decrease the output based on the skin tone determination. In one example, the one or more processors utilize a mathematical determination to determine the power output of the first and/or second light sources based on the detected increase in signals based on the reflected auxiliary light from the volume as the probe is moving toward the volume. Alternatively, the rate of increase of the signals detected from the reflected auxiliary light is compared to historical data in a lookup table, and based on the comparison, the output of the first and/or second primary light source is varied accordingly. Based on the feedback received by the detection device(s), the output of the first and/or second primary light sources may be varied accordingly. Because the determination of skin tone is based on the signals generated based on the reflection auxiliary light prior to contact between the probe and volume, variance can occur prior to actuation of the first and/or second light source. This ensures the quality of the image is enhanced regardless of skin tone or color, improving upon resultant images.

The present system and methods are described above with reference to block diagrams and operational illustrations of methods and devices comprising an optoacoustic probe. It is understood that each block of the block diagrams or operational illustrations, and combinations of blocks in the block diagrams or operational illustrations, may be implemented by means of analog or digital hardware and computer program instructions. These computer program instructions may be provided to a processor of a general purpose computer, special purpose computer, ASIC, FPGA or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used in this description and in the following claims, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds.

As used in this specification and the appended claims, the term "or" is generally employed in its sense including "and/or" unless the content clearly dictates otherwise.

The recitation herein of numerical ranges by endpoints includes all numbers subsumed within that range (e.g. 1 to 5 includes 1, 1.5, 2, 2.75, 3, 3.80, 4, and 5).

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the scope of the claims, each numerical parameter should at least be construed in light of the number of reported significant digits and by applying ordinary rounding techniques. Any numerical value, however, inherently contains certain errors necessarily resulting from the standard deviations found in their respective testing measurements.

Those skilled in the art will recognize that the methods and systems of the present disclosure may be implemented in many manners and as such are not to be limited by the foregoing example embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

What is claimed is:

1. An optoacoustic probe for optoacoustic imaging of a volume, the optoacoustic probe having a distal end operable to contact the volume and a proximal end, the optoacoustic probe comprising:
   at least one primary light source configured to generate light that is transmitted along a light path to generate optoacoustic return signals when the light reacts with the volume;
   a transducer assembly including a transducer configured to receive the optoacoustic return signals and an acoustic lens provided over the transducer;
   an optical window configured to carry the light along the light path to the volume;
   an auxiliary light source configured to constantly generate auxiliary light carried through the optical window to the volume during operation of the optoacoustic probe;
   a detection device configured to detect signals generated from the auxiliary light and the light generated by the at least one primary light source reflecting from the volume or the optical window; and
   a microcontroller including one or more processors, and a memory coupled to the one or more processors, wherein the memory stores program instructions, wherein the program instructions are executable by the one or more processors to:
      receive the signals generated from the auxiliary light reflecting from the volume including while the at least one primary light source generates the light;
      determine contact between the volume and the optoacoustic probe based on the signals generated from the auxiliary light reflecting from the volume;
      prevent the at least one primary light source from generating the light until the optoacoustic probe is contacting the volume.

2. The optoacoustic probe of claim 1, further comprising a triggering system configured to actuate the at least one primary light source and the auxiliary light source, and configured to prevent actuation of the at least one primary light source before actuation of the auxiliary light source.

3. The optoacoustic probe of claim 2, further comprising a foot actuator coupled to the triggering system; wherein responsive to actuation of the foot actuator, the triggering system actuates the auxiliary light source.

4. The optoacoustic probe of claim 1, wherein the auxiliary light source is a light emitting diode and the at least one primary light source is a laser.

5. The optoacoustic probe of claim 1, wherein the detection device is disposed adjacent the optical window.

6. The optoacoustic probe of claim 1, wherein the auxiliary light source is within a housing of the optoacoustic probe.

7. The optoacoustic probe of claim 1, wherein the auxiliary light source is within a laser head of the at least one primary light source.

8. The optoacoustic probe of claim 1, wherein the detecting device is at least one of a light sensor, thermopile, oxygen meter, piezoelectric sensor, spectrometer, digital camera, or charge couple device.

9. The optoacoustic probe of claim 1, wherein the signals generated from the auxiliary light reflecting from the volume are sound based signals.

10. A method of triggering a primary light source of an optoacoustic probe comprising:
  constantly actuating an auxiliary signal source within a probe housing to generate an auxiliary signal during operation of the optoacoustic probe, wherein the auxiliary signal that is generated is a light signal;
  detecting the auxiliary signal after the auxiliary signal has reflected from a volume;
  determining when the optoacoustic probe contacts the volume based on the auxiliary signal after the auxiliary signal has reflected from the volume;
  triggering the primary light source located outside the probe housing in response to determining the optoacoustic probe contacts the volume;
  preventing the primary light source from actuating in response to determining the optoacoustic probe is not contacting the volume; and
  wherein preventing the primary light source from actuating in response to determining the optoacoustic probe is not contacting the volume includes ignoring a command to actuate the primary light source based on the auxiliary signal detected.

11. The method of claim 10, wherein determining when the optoacoustic probe contacts the volume based on the auxiliary signal after the auxiliary signal has reflected from the volume includes determining an increase of reflected light based on the auxiliary signal after the auxiliary signal has reflected from the volume.

12. The method of claim 10, wherein actuating the auxiliary signal source includes actuating a foot actuator coupled to the auxiliary signal source.

13. The method of claim 10, wherein the auxiliary signal detected is one of a sound signal, piezo based signal, or ultrasound signal.

14. The method of claim 10, wherein receiving the auxiliary signal detected utilized to ignore the command to actuate the primary light source based on the auxiliary signal detected occurs while the primary light source generates light.

15. A method of triggering a primary light source of an optoacoustic probe comprising:
  constantly actuating an auxiliary light source to generate auxiliary light during operation of the optoacoustic probe;
  detecting signals generated from the auxiliary light reflecting from a volume;
  determining an increase of reflected light based on the signals detected as the optoacoustic probe moves toward the volume;
  determining when the optoacoustic probe contacts the volume based on the signals generated from the auxiliary light reflecting from the volume;
  varying an output of the primary light source in response to the increase of reflected light; and
  triggering the primary light source in response to determining the optoacoustic probe contacts the volume.

16. The method of claim 15, further comprising:
  comparing the determined increase of reflected light based on the signals detected as the optoacoustic probe moves toward the volume to historical data that includes increases of reflected light as the optoacoustic probe moves toward the volume for different volumes.

17. The method of claim 16, wherein varying the output of the primary light source in response to the increase of reflected light includes increasing the output based on the comparison of the determined increase of reflected light and the historical data.

18. An optoacoustic probe for optoacoustic imaging of a volume, the optoacoustic probe having a distal end operable to contact the volume and a proximal end, the optoacoustic probe comprising:
  at least one primary light source configured to generate light that is transmitted along a light path to generate optoacoustic return signals when the light reflects from the volume;
  a transducer assembly including a transducer configured to receive the optoacoustic return signals and an acoustic lens provided over the transducer;
  an optical window configured to carry the light along the light path to the volume; and
  an auxiliary light source configured to generate auxiliary light carried through the optical window to the volume;
  wherein the auxiliary light source is a light emitting diode and the at least one primary light source is a laser;
  wherein the auxiliary light source is within a housing of the optoacoustic probe; and the primary light source is located outside the housing of the optoacoustic probe;
  a detection device configured to detect signals generated from the auxiliary light reflecting from the volume; and
  a microcontroller including one or more processors, and a memory coupled to the one or more processors, wherein the memory stores program instructions, wherein the program instructions are executable by the one or more processors to:
  obtain the signals generated from the auxiliary light reflecting from the volume as the optoacoustic probe moves toward the volume;
  determine a skin characteristic based on the signals generated from the auxiliary light reflecting from the volume as the optoacoustic probe move toward the volume;
  in response to determining the skin characteristic based on the signals generated from the auxiliary light reflecting from the volume as the optoacoustic probe move toward the volume, vary an output of the at least one primary light source.

19. The optoacoustic probe of claim 18, wherein the skin characteristic is skin color.

* * * * *